US006285137B1

(12) United States Patent
Grossman et al.

(10) Patent No.: US 6,285,137 B1
(45) Date of Patent: Sep. 4, 2001

(54) MATERIALS TEST CHAMBER WITH XENON LAMP RADIATION

(75) Inventors: Douglas M. Grossman, Fairview Park; Kenneth A. Roll, Kirtland; Gregory Fedor, Bay Village, all of OH (US)

(73) Assignee: Q-Panel Lab Products Corp., Westlake, OH (US)

( * ) Notice: Subject to any disclaimer, the term of this patent is extended or adjusted under 35 U.S.C. 154(b) by 0 days.

(21) Appl. No.: 09/383,350

(22) Filed: Aug. 26, 1999

Related U.S. Application Data
(60) Provisional application No. 60/097,964, filed on Aug. 26, 1998.

(51) Int. Cl.$^7$ ............................................. G05F 1/00
(52) U.S. Cl. .................. 315/291; 315/360; 315/DIG. 4; 250/493.1; 250/504 R
(58) Field of Search .................. 315/291, 149, 315/150, 307, 360, DIG. 2, DIG. 4, DIG. 5, DIG. 7; 250/493.1, 494.1, 495.1, 504 R

(56) References Cited

U.S. PATENT DOCUMENTS

| | | | |
|---|---|---|---|
| 3,675,078 | * 7/1972 | Levy | 315/DIG. 5 |
| 3,686,940 | 8/1972 | Kockott | 73/150 |
| 3,953,763 | * 4/1976 | Herrick | 315/DIG. 7 |
| 4,012,954 | 3/1977 | Klippert | 73/150 R |
| 4,747,645 | 5/1988 | Rudzki | 350/1.1 |
| 4,884,009 | 11/1989 | Rothwell, Jr. et al. | 315/246 |
| 4,949,017 | * 8/1990 | Sikora | 315/DIG. 7 |
| 5,051,665 | * 9/1991 | Garrison et al. | 315/291 |
| 5,206,518 | 4/1993 | Fedor et al. | 250/504 R |
| 5,317,237 | * 5/1994 | Allison et al. | 315/307 |
| 5,442,261 | * 8/1995 | Bank et al. | 315/360 |
| 5,488,267 | 1/1996 | Rudolph et al. | 315/63 |
| 5,825,139 | * 10/1998 | Nuckolls et al. | 315/307 |
| 5,962,988 | * 10/1999 | Nuckolls et al. | 315/DIG. 4 |
| 5,982,112 | * 11/1999 | Pringle et al. | 315/DIG. 4 |
| 5,990,633 | * 11/1999 | Hirschmann et al. | 315/291 |
| 6,092,208 | * 7/2000 | Flory, IV | 315/DIG. 5 |

* cited by examiner

Primary Examiner—Don Wong
Assistant Examiner—Thuy Vinh Tran
(74) Attorney, Agent, or Firm—Fay, Sharpe, Fagan, Minnich & McKee, LLP

(57) ABSTRACT

A high-instantaneous, low-average current ballast is used in an accelerated weathering apparatus. The ballast includes a DC voltage generator or front end, to generate a high DC voltage, which produces a charging current to charge an arc capacitor. The energy on the arc capacitor is selectively released into a xenon lamp as short, high-current pulses. A starting transformer acts to strike an arc in the lamp. A switch is connected between the capacitor and the lamp, and is used to control generation of current pulses developed for the xenon lamp. A timer is implemented to control operation of the transformer and switch to selectively generate the current pulses for the xenon lamp.

24 Claims, 3 Drawing Sheets

MATERIALS TEST CHAMBER WITH XENON LAMP RADIATION

This application claims benefit of U.S. Provisional Application No. 60/097,964 filed Aug. 26, 1998.

BACKGROUND OF THE INVENTION

This invention pertains to the art of testing specimens for resistance to deterioration due to sunlight, and more particularly to a materials test chamber using discharge lamps such as xenon lamps for the light source.

This invention is particularly applicable to an accelerated weathering apparatus employing xenon lamps to simulate the deterioration of specimens caused by sunlight, and will be described with particular reference thereto. However, it will be appreciated that the application has broader applications and may be advantageously employed in connection with other lamps and devices.

U.S. Pat. No. 5,488,267, to Rudolph et al., discloses an illumination system for weathering and fading resistance test instruments. Provided is a pulse-driven xenon gas discharge lamp with an elongated discharge lamp that has an electrode spacing in a range from 10–50 cm. The duty factor of the lamp current is adjusted by means of an electronic control unit.

U.S. Pat. No. 4,747,645, to Rudzki discloses a weathering and fading resistance test instrument which provides for adjustment of the defined radiation spectrum that encompasses ultra-violet (UV) radiation, and infra-red (IR) radiation, by means of a xenon radiation source. Two sectors are provided for the radiation. The first sector includes UV mirrors that are impermeable to UV radiation, and a second sector includes a UV filter and at least one IR filter that are permeable to visible light. Each one of the sectors is associated with a corresponding xenon radiation source. The filter/radiation system is initially surrounded by a quartz inner cylinder with a selectively reflective layer for IR that is permeable to UV light, and an adjacent water jacket which absorbs longwave IR radiation, then by a quartz outer cylinder, and finally by a three-piece sealing jacket made of glass. This configuration is intended to dampen the intensity of a given spectral component in a targeted fashion, or to vary and set the ratio of the ultra-violet to the infra-red components.

Xenon lamps are known to operate efficiently at high-current density. Higher currents produce more light output per watt of electrical input. It is also believed that high current density also changes the shape of a Spectral Power Distribution (SPD) to produce more UV and less IR as a percent of total output. Such a result is considered to be useful for weathering testers.

In existing 50/60 hertz ballasts (or DC ballasts), high current is known to also produce extra wattage (heat) on the xenon lamp. This reduces the xenon lamp life, which is already known to have a substantially short life span. Furthermore, high current raises the total wattage consumption. Rudzki attempts to protect the xenon lamp by providing water cooling. It is noted that even with this water cooling protection, such machines will still have high wattage consumption. The system of Rudolph et al., describes an amplitude discharge current in the range of between 15 and 100 amps at a cold fill pressure of less than 400 mbar. The duty factor of such a device is from 1:1 to 1:100, and in a preferred embodiment the discharge current comprises pulses of alternating polarity, with the maximum duration of the current pulse noted as being 10 ms.

A drawback of existing devices, as noted above, is the rate of deterioration of the xenon lamp and the increased operation cost due to high power consumption. In view of this, existing accelerated weathering apparatuses which employ xenon discharge lamps have not been able to fully exploit the benefits which would be available by operating the xenon lamps at high current densities. The benefits of such operation xenon lamps include efficient operation, the production of more UV with less IR as a percentage of total lamp output.

Therefore, it has been deemed desirable to find a manner of operating an accelerated weathering apparatus employing a xenon lamp at very high current density. It is further desired that such operation does not shorten xenon lamp life, and allows for acceptable power consumption for weathering apparatuses employing xenon lamps.

SUMMARY OF THE INVENTION

The present invention contemplates a new and improved accelerated weathering apparatus that overcomes all of the above-noted problems and others, and provides for operation of a xenon lamp at a high level of efficiency.

According to another aspect of the invention, disclosed is a high instantaneous, low average current ballast for controlling operation of a xenon lamp. A DC voltage generator, or front end, acts to generate a high DC voltage. A capacitor is arranged to store energy developed from the charging action of the charging current, and to selectively release the capacitor energy to provide short, high-current pulses. A starting transformer acts to strike an arc in the xenon lamp. A switch connected between the capacitor and the lamp is used to control generation of the current pulses, and a timer controls operation of the starting transformer and switch for selectively generating and supplying the current pulses to the xenon lamp.

According to yet another aspect of the invention, a dimmer limits the energy level to which the capacitor is charged.

According to yet another aspect of the invention, the voltage on the capacitor is over 400 volts with a preferred operation over 600 volts, and the pulse current sent to the lamp is at least 100 amps.

A principle advantage of the invention is an accelerated weathering apparatus that operates at a high efficiency using a xenon lamp, wherein the xenon lamp does not overheat, and whose life expectancy is not diminished.

Another advantage of the invention resides in the improvement in the ratio of UV to IR by operating the xenon lamp at a high current level.

Still another advantage of the invention is realized by maintaining a low overall average current supplied to the xenon lamp.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, a preferred embodiment of which will be described in detail in the specification and illustrated in the accompanying drawings which form a part hereof and wherein.

DETAILED DESCRIPTION OF THE PREFERRED EMBODIMENT

Figure 1:
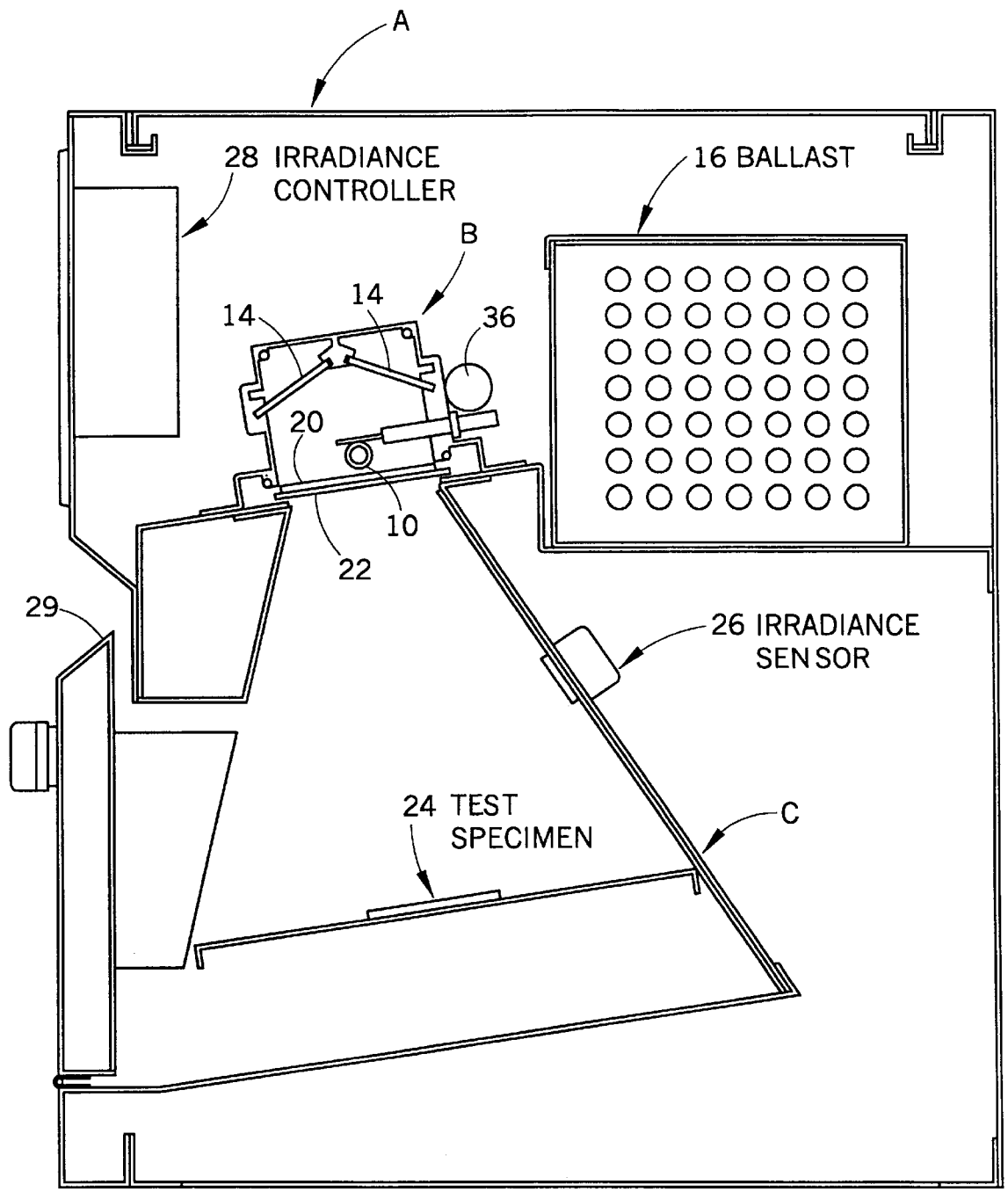
FIG. 1 illustrates an embodiment of the accelerated weathering apparatus of the present invention.

Referring now to the drawings wherein the showings are for the purposes of illustrating the preferred embodiment of the invention only, and not for purposes of limiting the same, the figures show an accelerated weathering apparatus implementing a high-instantaneous, low-average current ballast.

With reference to FIG. 1, depicted is a side view of an accelerated weathering apparatus A which includes lamp housing B, and specimen chamber C. While FIG. 1 is a side view of a one-lamp weathering apparatus, it is to be appreciated the present invention may be used in conjunction with accelerated weathering apparatuses which have multiple lamps.

Lamp housing B includes xenon lamp 10, which may be held by a lamp holder (not shown). Within lamp housing B, are ultra-violet (UV) reflectors 14 used to reflect light into specimen chamber C. A high-instantaneous, low-average current ballast 16 is used to cause xenon lamp 10 to be fired. As an option, infrared (IR) mirror 20 may be included to reflect back infra-red wavelength light, and a UV filter 22, which is a glass filter, may be used to filter out short wavelength ultra-violet light. The remaining light passes into specimen chamber C, wherein it acts on specimens 24. An irradiance sensor 26 measures the amount of light in specimen chamber C and provides this information to an irradiance controller 28, which adjusts the xenon lamp output in accordance with values set by a user via an input control panel (not shown). Test specimens 24 are placed into the test chamber through door 29, which is on a hinge type mechanism. An accelerated weathering apparatus employing examples of an irradiance controller and an input control panel are shown for example in U.S. Pat. No. 5,206,518 to Fedor et al., hereby incorporated by reference.

As previously discussed, xenon lamps are known to operate more efficiently at high current density, i.e. higher currents produce more light per watt of electrical input. It is also believed that high-current density has an added advantage of changing the shape of the Spectral Power Distribution (SPD) curve to produce more UV and less IR as a percent of total output. This attribute is beneficial in the area of accelerated weather testing. It is also known, however, that injecting high current into a xenon lamp produces extra wattage (heat) on the xenon lamp, which acts to reduce xenon lamp life expectancy. Additionally, the high current raises wattage consumption of the accelerated weathering apparatus.

In the present invention, high-instantaneous, low-average current ballast 16, is used to operate xenon lamp 10 at high current for a short time period and then acts to quickly shut off xenon lamp 10 for an extended period. By such operation, when xenon lamp 10 is in an "on" state, it operates at a high current density, however, because it spends the majority of its time in an "off" state, the average current feed to xenon lamp 10 is much lower, and overall wattage consumption is lower than would exist if a longer "on" state were used.

In a preferred embodiment, high-instantaneous, low-average current ballast 16 is designed to run a 15 inch long, low pressure xenon arc lamp. It is to be appreciated the invention can also be implemented with other sized ballasts. Ballast 16 is capable of running the xenon lamp at 1800 watts but is normally dimmed for alternative light outputs. For 1800 watts operation, ballast 16 achieves the desired operation by pulsing xenon lamp 10 through a capacitive discharge of approximately 200 amps peak current, for 300 $\mu$seconds duration. In this embodiment, the discharge is repeated nominally at 112.5 times a second. The capacitor provided is a 50 $\mu$farad charged to 800 V. Therefore, the calculated power is $P=CV^2f/2=(50\times10-6)(800)^2(112.5)/2=1800$ w. It is to be appreciated that if xenon lamp is to be dimmed, one manner in which to accomplish this is to lower the energy stored on the capacitor.

Figure 2:
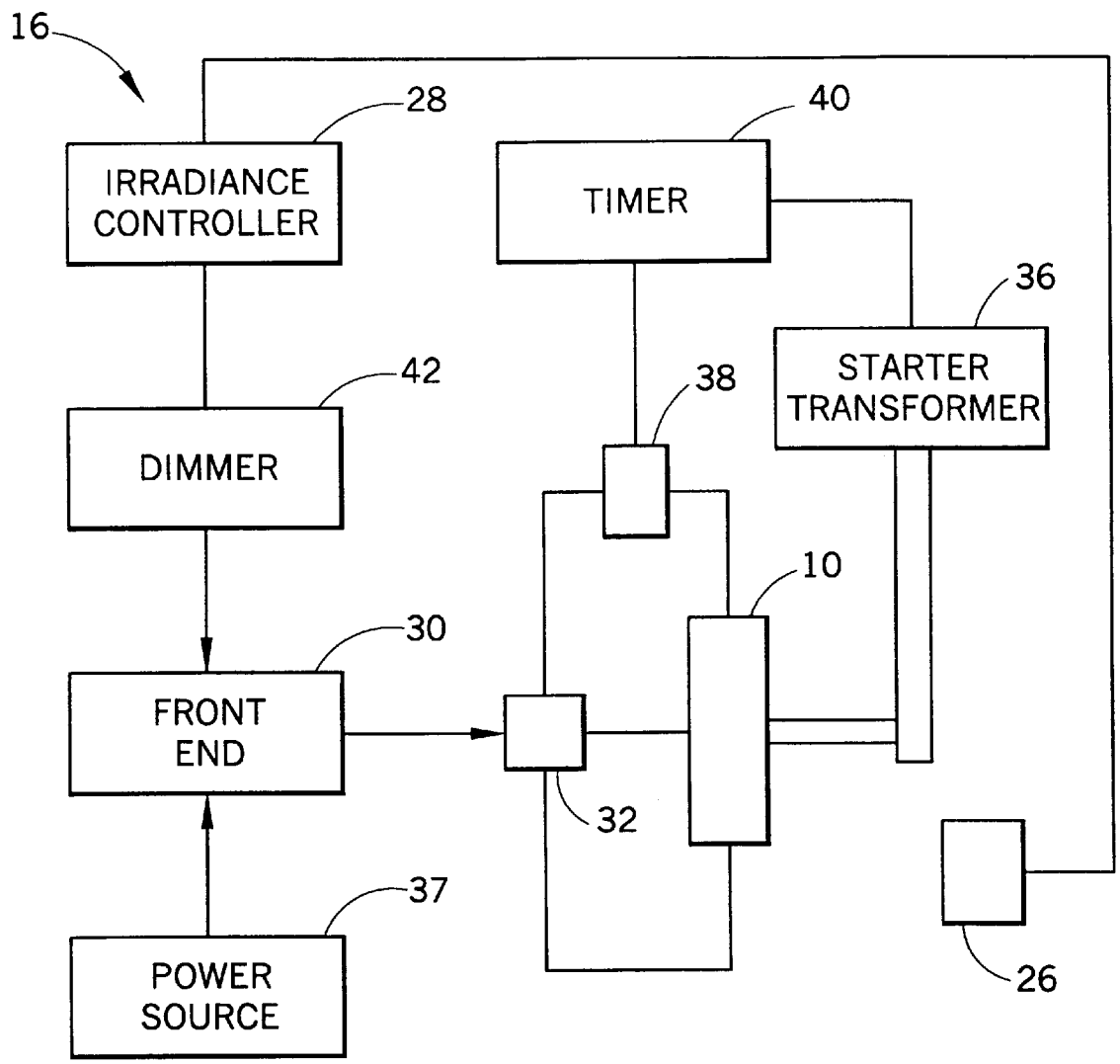
FIG. 2 is a block diagram showing operation of the high-instantaneous, low-average current ballast for control of the xenon lamp.

Turning attention to FIG. 2, ballast 16 includes a power factor corrected front end 30, that produces a high DC voltage. Arc capacitor 32 stores energy and releases it into xenon lamp 10 as short, high current pulses. In one embodiment starting transformer 36 generates a high voltage which facilitates starting of the arc. It is noted other starting techniques are available such as series injection. Front end 30 is supplied by a known power source 37, such as power lines, etc.

Ballast 16 also includes switch 38, such as a transistor switch, located between arc capacitor 32 and xenon lamp 10. When switch 38 is in an "on" state, a high current pulse is delivered to xenon lamp 10. When switch 38 is in an "off" state, current flow is blocked, thereby allowing a build-up of energy on arc capacitor 32, without leakage current to xenon lamp 10.

Timer 40 controls operation of starter transformer 36 and switch 38 such that current pulses controlling operation of xenon lamp 10 are provided at a controlled frequency.

Dimmer 42, through front end 30, limits the energy being supplied to arc capacitor 32 thereby controlling illuminance of xenon lamp 10. Dimmer 42 may be configured to control dimming by pulse width modulation. An alternative would be for timer 42 to shut off charging of capacitor 32, prior to reaching a predetermined energy level.

Additionally, irradiance controller 28 receives signals from irradiance sensor 26, and adjusts dimmer 42 in accordance with the received signals in order to maintain a preselected output from xenon lamp 10. It is noted that in FIG. 2 irradiance controller 28 is depicted as part of ballast 16.

As discussed, a concept of the present invention is to use a high-instantaneous, low-average current ballast 16 to run xenon lamp 10 at extremely high current for a minimal amount of time, then quickly switch to an "off" state which is much longer than the "on" state. Under these conditions, whenever xenon lamp 10 is "on", it will be operating at a high-current density. However, as the majority of its time is spent in an "off" state, the average current through xenon lamp 10 is much lower than the peak current, thereby providing for low overall wattage consumption.

Figure 3:
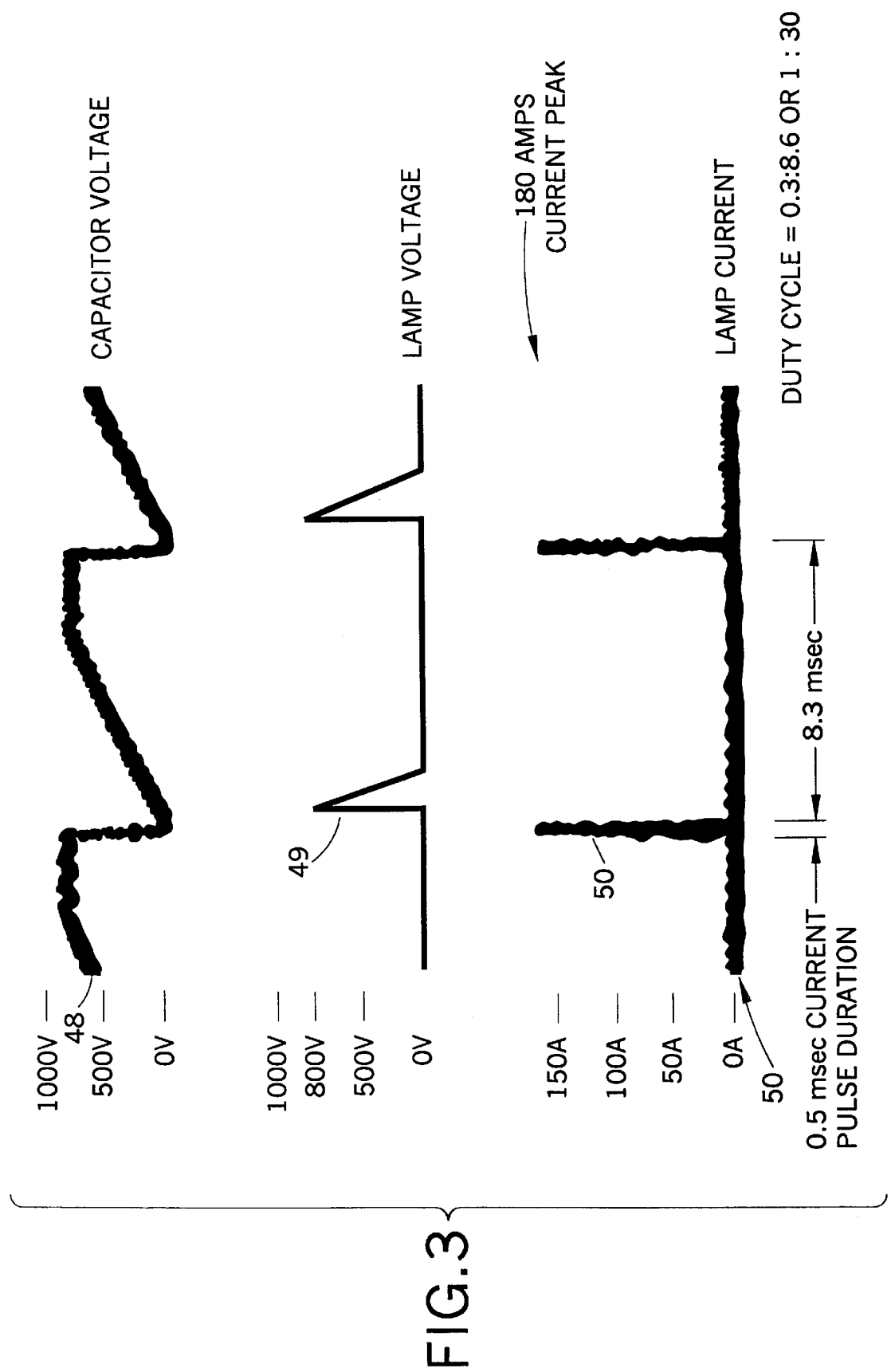
FIG. 3 is capacitor voltage, lamp voltage and lamp current wave forms in accordance with the teachings of the present invention.

The preceding concept is further illustrated in FIG. 3 which depicts measured voltage and current wave forms. Particularly, capacitor voltage wave form 48 shows that voltage to xenon lamp 10 will peak at greater than 600 volts, and preferably approximately 800 volts, and following discharge will again charge up to its peak energy level. Lamp current wave form 50 illustrates that for a 8.6 ms cycle signal, the current pulse generated from the energy on arc capacitor 32, is supplied to xenon lamp 10 for 0.3 ms, which is the "on" time of xenon lamp 10. The value of the 0.3 ms current pulse is approximately 180 amps. Lamp voltage wave form 49 is also shown, and is noted to substantially correspond to the current pulses of wave form 50. For the remaining time, i.e. approximately 8.3 ms. of the cycle, xenon lamp 10 is in an "off" state. Thus, the average current across xenon lamp 10 is minimal compared to the peak current of approximately 180 amps. Under the design of the present invention, the life of xenon lamp 10 is not detrimentally shortened and the wattage consumption of the device is minimized.

Operation of the high instantaneous, low average current ballast 16 includes initially generating a high DC voltage and power factor corrected front end 30. This action causes arc capacitor 32 to begin charging to a desired voltage level. During the charging up period, switch 38 is in an inhibit state whereby arc capacitor 32 is not connected to xenon lamp 10. Once arc capacitor 32 has reached a desired energy level, timer 40 can then send a signal to move switch 38 to an "on" state, which will connect charged arc capacitor 32 to xenon lamp 10, through switch 38. Starting transformer 36, whose operation is also controlled by timer 40, is fired thereby generating a voltage field at xenon lamp 10. This action causes the ionization of gases in xenon lamp 10. A high short duration pulse current is delivered to xenon lamp 10 from capacitor 32 through the current path formed by arc capacitor 32, switch 38 and xenon lamp 10. Following a prescribed time period, timer 40 sets switch 38 to an inhibit, "off", state thereby opening the current path between arc capacitor 32 and xenon lamp 10.

It is noted that power factor corrected front end 30 is asynchronous and independent of timer 40.

With further attention to arc capacitor 32, its energy rating is required to be high enough to withstand the energy received from the front end. The capacitance must be large enough to contain enough energy for each lamp pulse but small enough that the capacitor can be recharged quickly before the next pulse, and small enough that a rate of 112.5 pulses/sec will not add up to more wattage than the xenon lamp can handle. The energy stored in a capacitor is equal to capacitance times the square of voltage: $E=1/2CV^2$. It is to be appreciated that different sized capacitors may be used, depending upon the particular capabilities desired for an apparatus.

Starting transformer 36 may be designed to strike an arc with a 10 kV trigger transformer, which is run by the discharge from a capacitor controlled by an IGBT or an SCR. This circuit operates with minimal current. The high voltage ionizes the gases of the xenon lamp just by being in close proximity thereto.

It is to be appreciated, however, that there are other arrangements which may be used for striking the arc of the xenon lamp. Particularly, a conductive material may be wrapped around the lamp and the voltage applied in this manner. Another procedure would be to strike the arc via "series injection", which requires a large, high-voltage high-current transformer to strike the arc through the transformer terminals.

With further attention to switch 38, in one embodiment it is anticipated that a transistor is used to perform the functions of switching and to prevent arc operation at inefficient, low-current densities. After the arc extinguishes itself switch 38 keeps the arc from restriking until the capacitor is fully recharged.

Returning to timer 40, in addition to the discussion of operation previously set forth, under certain conditions it may be desired to provide a pulsing frequency of greater than 60 times per second, and preferably at least 100 times per second, appropriate pulsing must be maintained even at a lowest dimming level, since pulsing too slow may cause visible flickering.

Dimmer 42 has also been disclosed as being used to adjust the amount of energy supplied to the discharge capacitor based on the irradiance sensed by irradiance sensor 26. However, dimming may also be controlled by changing the frequency of pulses so that dimming of xenon lamp 10 is achieved by providing 90, 80, 70 or 60 pulses instead of the 100 or more pulses per second previously discussed.

It is noted that a new xenon lamp will have a higher efficiency than an older xenon lamp. Therefore, when a new xenon lamp is used, dimming will assist in achieving the desired irradiance of the specimens. As the xenon lamp ages, less dimming is used to offset the lowered efficiency of the xenon lamp.

It is also noted that weathering procedures for different specimens may vary, requiring different irradiance values. Specimens may also be measured at different wavelengths. Common weathering wavelengths are 0.35 w/sq meters at 340 nanometers wavelength; 0.55 w/sq meters at 340 nanometers wavelength; and 0.68 w/sq meters at 340 nanometers wavelength.

The xenon lamp 10 being used in one embodiment may be a straight xenon lamp having a lamp arc length of 31.1 cm. The inside diameter of the lamp is 8.1 mm and the cold fill pressure is approximately 130 mbar. In the embodiment shown in FIG. 3, the duty cycle was set at 1:30 (though other duty cycles may be used, such as 1:10, 1:15, 1:20, etc.), the current pulse amplitude was shown as being 180 amps with a current pulse duration of ms. The device used has a non-altering pulse polarity, i.e. direct current, to the lamp and a discharge current frequency set at 100 pulses per second or more. Under this design, the current pulses average less than 20 amps over a full signal, where there is a duty cycle of 1:100 or less. It is to be appreciated that while the discussion has focused on a xenon lamp of this type other sized xenon lamps may be used as well as another types of discharge lamps.

The invention has been described with reference to the preferred embodiment. Obviously modifications and alterations will occur to others upon a reading and understanding of this specification. It is intended to include all such modifications and alterations in so far as they come within the scope of the appended claims or the equivalence thereof.

What is claimed is:

1. An accelerated weathering apparatus comprising:
   a test chamber having a support member to support a specimen which is to be tested;
   a lamp for producing light in the test chamber; and
   a high instantaneous, low average current ballast for controlling operation of the lamp wherein the ballast generates current pulses, at least some of the current pulses being at least 100 amps, said current pulses having averages of less than 20 amps over a full signal.

2. The invention according to claim 1 wherein the ballast includes:
   a front end, supplied by an external power source, which generates high DC voltage;
   an arc capacitor connected to store energy developed from charging action of the front end and to selectively release the arc capacitor energy into the lamp as short, high current pulses;
   a starting transformer that generates a voltage used to ionize gas in the lamp to strike an arc;
   a switch connected between the arc capacitor and the lamp and used to control generation of the current pulses; and an internal or external timer to control the switch and transformer for selectively generating and supplying of the current pulses to the lamp.

3. The accelerated weathering apparatus according to claim 1, wherein there is a duty cycle of 1:10 or less.

4. The accelerated weathering apparatus according to claim 1 wherein the voltage on the arc capacitor is 500 volts or more.

5. The accelerated weathering apparatus according to claim 1 wherein the current pulses are delivered to the lamp at a rate of at least 60 per second.

6. The accelerated weathering apparatus according to claim 1 wherein the lamp is a xenon.

7. The invention according to claim 1 wherein the xenon lamp is supplied with a pulse of less than 1 ms duration.

8. An accelerated weathering apparatus comprising:
a test chamber having a support member to support a specimen which is to be tested;
a lamp for producing light in the test chamber;
a high instantaneous, low average current ballast for controlling operation of the lamp wherein the ballast generates current pulses, at least some of the current pulses being at least 100 amps; and
dimming circuitry designed to limit energy transfer from the capacitor into the lamp.

9. A method of operating a high instantaneous, low average current ballast which controls a xenon lamp, said method comprising the steps of:
generating a high DC voltage to charge a capacitor to a desired level;
connecting the charged capacitor to the xenon lamp, through a switch;
firing a starting transformer which generates a voltage field at the xenon lamp, thereby ionizing gases in the xenon lamp;
forming a main current path including the charged capacitor, the switch, and the xenon lamp, said switch being disposed between and in series with the charged capacitor and the xenon lamp;
delivering current to the xenon lamp through the main current path; and
opening the switch so that the capacitor is again disconnected from the xenon lamp and charged up to the desired value.

10. The method of operating a high instantaneous, low average current ballast which controls a xenon lamp according to claim 9, wherein the current delivered to the xenon lamp are current pulses, at least some of the current pulses being at least 100 amps, said current pulses having an average of less than 20 amps over a full signal.

11. The method of operating a high instantaneous, low average current ballast which controls a xenon lamp according to claim 10, wherein there is a duty cycle of 1:10 or less.

12. The method of operating a high instantaneous, low average current ballast which controls a xenon lamp according to claim 10, wherein the method further includes supplying the current pulses to the xenon lamp at a rate of at least 60 per second.

13. The method of operating a high instantaneous, low average current ballast which controls a xenon lamp according to claim 10, wherein the method further includes charging the capacitor to 500 volts or more.

14. A method of operating a high instantaneous, low average current ballast which controls a xenon lamp, said method comprising the steps of:

generating a high DC voltage to charge a capacitor to a desired level;
connecting the charged capacitor to the xenon lamp, through a switch;
firing a starting transformer which generates a voltage field at the xenon lamp, thereby ionizing gases in the xenon lamp;
forming a current path including the charged capacitor, the switch, and the xenon lamp;
delivering current to the xenon lamp through the current path;
opening the switch so that the capacitor is again charged up to the desired value;
using dimming circuitry, limiting energy transfer from the capacitor into the lamp.

15. An accelerated weathering apparatus comprising:
a specimen chamber configured to hold a specimen;
a xenon lamp;
a high-instantaneous, low-average current ballast configured to run the xenon lamp including,
a front end, that produces a high DC voltage,
an arc capacitor designed to store energy and release the energy into the xenon lamp as short, high current pulses,
a starting transformer which generates a high voltage which facilitates striking an arc in the xenon lamp,
a switch located between the arc capacitor and the xenon lamp, wherein when the switch is in an on state, a high current pulse is generated from the energy on the arc capacitor, and is delivered to the xenon lamp, and when the switch is in an off state, current flow is blocked thereby allowing a build-up of the arc capacitor energy, without leakage to the xenon lamp,
a dimmer configured to limit the energy being supplied from the arc capacitor,
thereby controlling light output of the xenon lamp;
an irradiance sensor, which measures the amount of light in the specimen chamber; and
an irradiance controller, which receives signals from the irradiance sensor, and adjusts a dimmer in accordance with the received signals, in order to maintain a preselected output from the xenon lamp.

16. The invention according to claim 15 further including a timer configured to control operation of the starter transformer and the switch such that current pulses controlling operation of the xenon lamp are provided at a controlled frequency.

17. The invention according to claim 16 wherein the current pulses over a full signal average less than 20 amps, where there is a duty cycle of 1:10 or less.

18. The invention according to claim 15 wherein the current pulse delivered to the xenon lamp is at least 100 amps.

19. The invention according to claim 15 wherein the xenon lamp has a peak voltage of over 600 volts.

20. The invention according to claim 15 wherein the dimmer limits the energy being supplied to the arc capacitor, thereby controlling illuminance of the xenon lamp.

21. A current ballast which controls a xenon lamp, said ballast comprising:
a front end, supplied by an external power source, which generates high DC voltage;
an arc capacitor connected to store energy developed from charging action of the front end and to selectively release the arc capacitor energy in the lamp as current pulses, at least some of the current pulses being at least 100 amps at a rate of at least 60 per second, wherein the current pulses average less than 20 amps over a full signal;

a starting transformer that generates a voltage used to ionize gas in the lamp to strike an arc;

a switch connected between the arc capacitor and the lamp used to control generation of the current pulses; and an internal or external timer to control the switch and transformer for selectively generating and supplying of the current pulses to the lamp.

22. The current ballast of claim 21 further comprising:

dimming circuitry designed to limit energy transfer from the capacitor into the lamp.

23. A method of operating a current ballast which controls a xenon lamp, the method comprising the steps of:

generating a high DC voltage to charge a capacitor to a desired level;

connecting the charged capacitor to the xenon lamp through a switch;

forming a current path including the charged capacitor, the switch, and the xenon lamp;

delivering current pulses, at least some of the current pulses being at least 100 amps to the xenon lamp through the current path, said current pulses having a full signal average of less than 20 amps.

24. The method according to claim 23, wherein the current pulses are delivered to the lamp at a rate of at least 60 per second.

* * * * *